United States Patent
Daidone et al.

(10) Patent No.: US 10,093,621 B2
(45) Date of Patent: Oct. 9, 2018

(54) 4-OXO-N-(4-HYDROXYPHENYL)RETINAMIDE DERIVATIVES AS THERAPEUTIC AGENTS FOR THE TREATMENT OF CANCER

(71) Applicants: FONDAZIONE IRCCS ISTITUTO NAZIONALE DEI TUMORI, Milan (IT); UNIVERSITA' DEGLI STUDI DI MILANO, Milan (IT)

(72) Inventors: Maria Grazia Daidone, Milan (IT); Valentina Appierto, Milan (IT); Paola Tiberio, Busto Arsizio (IT); Sabrina Dallavalle, Vimercate (IT); Loana Musso, Pozzuolo Martesana (IT); Elisa Niccolini, Certaldo (IT)

(73) Assignee: FONDAZIONE IRCCS INSTITUTO NAZIONALE DEI TUMORI, Milan (IT)

( * ) Notice: Subject to any disclaimer, the term of this patent is extended or adjusted under 35 U.S.C. 154(b) by 14 days.

(21) Appl. No.: 15/510,798

(22) PCT Filed: Sep. 16, 2015

(86) PCT No.: PCT/EP2015/071178
§ 371 (c)(1),
(2) Date: Mar. 13, 2017

(87) PCT Pub. No.: WO2016/042010
PCT Pub. Date: Mar. 24, 2016

(65) Prior Publication Data
US 2017/0253560 A1   Sep. 7, 2017

(30) Foreign Application Priority Data

Sep. 17, 2014  (IT) .............................. MI2014A1603

(51) Int. Cl.
| | |
|---|---|
| *C07C 251/50* | (2006.01) |
| *C07C 403/18* | (2006.01) |
| *C07C 403/20* | (2006.01) |
| *A61K 31/167* | (2006.01) |
| *A61K 31/15* | (2006.01) |
| *A61K 45/06* | (2006.01) |

(52) U.S. Cl.
CPC .......... *C07C 403/20* (2013.01); *A61K 31/167* (2013.01); *A61K 45/06* (2013.01); *C07C 2601/16* (2017.05)

(58) Field of Classification Search
CPC ... C07C 251/50; C07C 403/18; C07C 403/20; A61K 31/167; A61K 31/15
USPC .......... 564/265, 271; 514/641, 640
See application file for complete search history.

(56) References Cited

U.S. PATENT DOCUMENTS

2003/0232820 A1   12/2003   Wolfe et al.
2013/0012591 A1   1/2013    Butler et al.

FOREIGN PATENT DOCUMENTS

WO   03018565 A1   3/2003
WO   2005092314 A1   10/2005

OTHER PUBLICATIONS

Laszlo Nagy, et al., Retinoid-induced apoptosis in normal and neoplastic tissues, Cell Death and Differentiation, Jan. 1998, pp. 11-19, vol. 5, No. 1, Stockton Press.
Umberto Veronesi, et al., Randomized Trial of Fenretinide to Prevent Second Breast Malignancy in Women With Early Breast Cancer, Journal of the National Cancer Institute, Nov. 3, 1999, pp. 1847-1856, vol. 91, Issue 21.
Fausto Chiesa, et al., Randomized trial of fenretinide (4-HPR) to prevent recurrences, new localizations and carcinomas in patients operated on for oral leukoplakia: Long-term results, International Journal of Cancer, 2005, pp. 625-629, vol. 115, Issue 4, Wiley-Liss, Inc.
Daniele Moglia, et al., Effects of topical treatment with fenretinide (4-HPR) and plasma vitamin A levels in patients with actinic keratoses, Cancer Letters, 1996, pp. 87-91, vol. 110, Issues 1-2, Elsevier Scientific Publishers Ireland Ltd.
Nicoletta Tradati, et al., Successful topical treatment of oral lichen planus and leukoplakias with fenretinide (4-HPR), Cancer Letters, 1994, pp. 109-111, vol. 76, Issue 2, Elsevier Scientific Publishers Ireland Ltd.
U. Veronesi, et al., Fifteen-year results of a randomized phase III trial of fenretinide to prevent second breast cancer, Annals of Oncology, Jul. 2006, pp. 1065-1071, vol. 17, No. 7.
(Continued)

*Primary Examiner* — Matthew P Coughlin
*Assistant Examiner* — Sagar Patel
(74) *Attorney, Agent, or Firm* — Young & Thompson

(57) ABSTRACT

The present invention relates to a compound having formula (I) below or a pharmaceutically acceptable salt thereof:

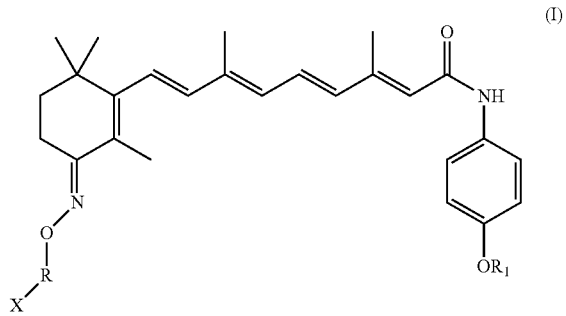

wherein:
X is —COOH or $NH_2$;
R is a straight or branched $C_1$-$C_{10}$ alkylene chain; and
$R_1$ is H, straight or branched $C_1$-$C_{10}$ alkyl, aryl, or $R_2CO$— wherein $R_2$ is straight or branched $C_1$-$C_{10}$ alkyl, for use as antitumoral agents.

18 Claims, 3 Drawing Sheets

(56) References Cited

OTHER PUBLICATIONS

Giuseppe De Palo, et al., Effect of Fenretinide on Ovarian Carcinoma Occurrence, Gynecologic Oncology, 2002, pp. 24-27, vol. 86.
N. Hail Jr., et al., Mechanisms of fenretinide-induced apoptosis, Apoptosis, Oct. 2006, pp. 1677-1694, vol. 11, Issue 10, Springer.
Maria Grazia Villani, et al., Identification of the Fenretinide Metabolite 4-Oxo-Fenretinide Present in Human Plasma and Formed in Human Ovarian Carcinoma Cells through Induction of Cytochrome, Clinical Cancer Research, Sep. 15, 2004, pp. 6265-6275, vol. 10.
Maria Grazia Villani, et al., 4-Oxo-Fenretinide, a Recently Identified Fenretinide Metabolite, Induces Marked G2-M Cell Cycle Arrest and Apoptosis in Fenretinide-Sensitive and Fenretinide-Resistant Cell Lines, Clinical Cancer Research, Mar. 15, 2006, pp. 3238-3247, vol. 66.
V. Appierto, et al., Analysis of gene expression identifies PLAB as a mediator of the apoptotic activity of fenretinide in human ovarian cancer cells, Oncogene, 2007, pp. 3952-3962, vol. 26, Nature Publishing Group.
Valentina Appierto, et al., PLAB induction in fenretinide-induced apoptosis of ovarian cancer cells occurs via a ROS-dependent mechanism involving ER stress and JNK activation, Carcinogenesis, 2009, pp. 824-831, vol. 30, No. 5, Oxford University Press.
Paola Tiberio, et al., 4-oxo-N-(4-hydroxyphenyl)retinamide: Two Independent Ways to Kill Cancer Cells, Plos One, Oct. 2010, pp. 1-11, vol. 5, Issue 10.
Jyoti B. Patel, et al., Novel Retinoic Acid Metabolism Blocking Agents Endowed with Multiple Biological Activities Are Efficient Growth Inhibitors of Human Breast and Prostate Cancer Cells in Vitro and a Human Breast Tumor Xenograft in Nude Mice, Journal of Medicinal Chemistry, 2004, pp. 6716-6729, vol. 47, No. 27.
Saul Wolfe, et al., Cyclic hydroxamates, especially multiply substituted [1,2]oxazinan-3-ones, Canadian Journal of Chemistry, 2003, pp. 937-960, vol. 81, Issue 8.
Jan. 19, 2016, International Search Report issued for related International Application No. PCT/EP2015/071178.

Antiproliferative activity of the combined treatment of salt 1a with a) paclitaxel (PTX), b) cisplatin (DDP), or c) fenretinide (4-HPR).
Ass= combination of the two compounds.

*In vivo* antitumor activity of salt 1a in a) mesothelioma cells (STO); b) ovarian cancer cells (IGROV-1); and c) breast cancer cells (MDA-MB-231).

4-OXO-N-(4-HYDROXYPHENYL)RETINAMIDE DERIVATIVES AS THERAPEUTIC AGENTS FOR THE TREATMENT OF CANCER

The present invention relates to 4-oxo-fenretinide derivatives, formulations containing them, and their use in the prevention and treatment of cancer, either alone or in combination with other compounds.

Retinoids are natural and synthetic derivatives of vitamin A (retinol) which modulate various cell processes, such as proliferation, differentiation and apoptosis. The synthetic retinoid fenretinide or N-(4-hydroxyphenyl)retinamide (4-HPR) (Nagy L. et al., *Cell Death Differ* 5: 11-19; 1998) is a non-toxic analogue of All-Trans Retinoic Acid (ATRA), (Veronesi U. et al., *J Natl Cancer Inst* 91: 1847-1856; 1999) which has given promising results for preneoplastic (Chiesa F. et al., *Int J Cancer* 115: 625-629; 2005; Moglia D. et al. *Cancer Lett* 110: 87-91; 1996; Tradati N et al., 1994) and neoplastic disorders (Veronesi U. et al., *Ann Oncol* 17: 106-171; 2006; De Palo G. et al., *Gynecol Oncol* 86: 24-27; 2002). Studies conducted in vitro have demonstrated that 4-HPR inhibits growth and induces apoptosis in tumour cell lines of various histotypes, and various mechanisms have been proposed, such as the generation of reactive oxygen species (ROS) and the consequent oxidative stress (Hail N. et al., *Apoptosis* 11:1677-1694; 2006; Appierto V. et al., *Carcinogenesis* 30:824-831; 2009).

4-oxo-N-(4-hydroxyphenyl)retinamide or 4-oxo-4-HPR is a natural polar metabolite of 4-HPR, identified in plasma samples of 4-HPR-treated patients and in the medium of 4-HPR-treated cancer cells (Villani M. G. et al., *Clin Cancer Res* 10:6265-75; 2004). 4-oxo-4-HPR elicits antiproliferative and apoptotic effects in various cancer cell lines (i.e., neuroblastoma, ovarian and breast cancer cell lines) and it is two to four times more effective than 4-HPR in inhibiting cell growth. Interestingly, 4-oxo-4-HPR is also effective in 4-HPR-resistant cancer cells and, in combination with 4-HPR, displays a synergistic effect (Villani M. G. et al., *Cancer Res* 66: 3238-47; 2006). The molecular studies have demonstrated that 4-oxo-4-HPR antitumor effect is due to at least two independent mechanisms of action: 1) 4-oxo-4-HPR, unlike 4-HPR and other retinoids, inhibits tubulin polymerization, causing a marked accumulation of cells in mitotic phase, coupled with aberrant spindle formation (i.e., multipolar organization without loss of centrosome integrity). 2) On the other hand, similarly to 4-HPR, 4-oxo-4-HPR causes apoptosis through a ROS-related signaling cascade involving endoplasmic reticulum (ER) stress response, activation of Jun N-terminal Kinase (AK) and PLAcental Bone morphogenetic protein (PLAB) upregulation (Appierto V. et al., *Oncogene;* 26:3952-62; 2007; Appierto V. et al., *Carcinogenesis* 30:824-31; 2009; Tiberio P. et al. *PLoS One;* 5(10):e13362; 2010).

The ability of 4-oxo-4-HPR to act through at least two unrelated mechanisms could provide an explanation of the ability of the retinoid to be more potent than the parent drug and could probably allow counteracting the development of drug resistance. Moreover, this distinctive mode of action may allow 4-oxo-4-HPR to target different types of human tumors more efficiently than 4-HPR. In addition, the combined treatment of 4-oxo-4-HPR with other anti-microtubule agents (such as vinca alkaloids and taxanes, which possess high toxicity and against which resistance easily develops) or conventional chemotherapeutic drugs could allow to decrease the doses of these agents and then to reduce their side effects.

However, 4-oxo-4-HPR presents very low solubility, and very low and highly variable plasma concentrations of the retinoid were found in experiments conducted in vivo, impairing the result reproducibility and its possible clinical use.

The derivatives according to the invention possess increased solubility in biological fluids and therefore better bioavailability, while maintaining the cytotoxic activity and mechanisms of action of 4-oxo-4-HPR.

The present invention relates to compounds having formula (I) below and the pharmaceutically acceptable salts thereof:

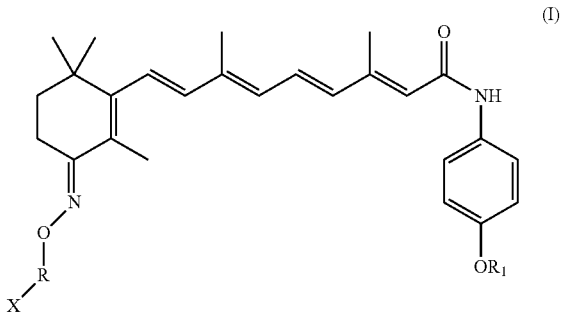

wherein:

X is —COOH or NH2, preferably —COOH;

R is a straight or branched $C_1$-$C_{10}$ alkylene chain, preferably a straight or branched $C_1$-$C_6$ alkylene chain, more preferably —$CH_2$—;

$R_1$ is H, straight or branched $C_1$-$C_{10}$ alkyl, preferably $C_1$-$C_6$, aryl, or $R_2$CO— wherein $R_2$ is straight or branched $C_1$-$C_{10}$ alkyl, preferably $C_1$-$C_6$, or aryl.

"Straight or branched $C_1$-$C_{10}$ alkylene chain" means a bivalent alkyl chain having 1 to 10 carbon atoms, such as —$(CH_2)_n$— wherein n is an integer from 1 to 10, or branched chains such as —$CH_2$—$CH(CH_3)$—$CH_2$—, —$CH(CH_3)$—$CH_2$—, —$CH(CH_3)$—$CH_2$—$CH_2$— and the like.

Said "alkylene chain" can optionally be replaced with one or more substituents, such as hydroxyl, halogen, amino and the like.

R is preferably a straight $C_1$-$C_6$ alkylene chain, more preferably —$CH_2$—.

The term "straight or branched $C_1$-$C_{10}$ alkyl" refers to a straight or branched alkyl group having 1 to 10 carbon atoms.

The term "straight or branched $C_1$-$C_6$ alkyl" refers to a straight or branched alkyl group having 1 to 6 carbon atoms such as methyl, ethyl, n-propyl, isopropyl, n-butyl, tert-butyl, isobutyl, n-pentyl, isopentyl, n-hexyl and the like.

Said "alkyl" can optionally be substituted with one or more substituents such as hydroxyl, halogen, amino and the like.

The term "aryl" refers to an aromatic carbocyclic group having 6 to 14 carbon atoms and a single ring (such as phenyl), or several rings, such as naphthyl, phenanthrenyl, biphenyl and the like. Said "aryl" can have 1 to 3 substituents, selected from hydroxyl, halogen, haloalkyl, cyano, $C_1$-$C_4$ alkyl, $C_1$-$C_4$ alkoxy and the like.

$R_1$ is preferably H.

Pharmaceutically acceptable salts of the compounds of Formula (I) wherein X is —COOH are either those with inorganic bases, such as sodium, potassium, lithium, calcium and magnesium hydroxides, or with appropriate organic amines or amino acids, such as arginine or procaine salts. The sodium salt is particularly preferred.

Pharmaceutically acceptable salts of the compounds of Formula (I) wherein X is —$NH_2$ are those with an appropriate acid, e.g. hydrochloric, sulphuric, phosphoric, maleic, fumaric, citric, tartaric, lactic, acetic or p-toluenesulphonic acid.

The preferred compounds are:

Compound 1a:

Sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxyacetate (sodium 4-aminooxyacetate-4-HPR);

Compound 1b (LOM1098):

Sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxybutyrate or butanoate (sodium 4-aminooxybutyrate-4-HPR);

Compound 1c (LOM1133):

Sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxyhexanoate (sodium 4-aminooxyhexanoate-4-HPR);

The present invention comprises all the possible stereoisomers and the racemic or optically active mixtures thereof.

The compounds according to the present invention present an antimitotic activity that makes them particularly interesting for the treatment of highly proliferating tumours. Moreover, the compounds according to the invention maintain the dual mechanism of action of 4-oxo-4-HPR, and can therefore be used to treat drug-resistant tumours.

The compounds according to the present invention can be used as antitumoral drugs for different tumours and, specifically, for actively proliferating solid and haematological tumours (either metastatic or not) and/or drug-resistant tumours, including but not limited to breast cancer, ovarian cancer, prostate cancer, colorectal cancer, mesothelioma and other sarcomas, neuroblastoma, lymphoma, leukaemia and melanoma.

In clinical trials it has been observed that retinol derivatives (such as fenretinide) cause less toxicity than the classic chemotherapy agents, and the preliminary data obtained in vivo with the sodium 4-aminoxyacetate-4-HPR salt (1a) seem to demonstrate that the toxicity of this compound is also not severe.

A further object of the invention is the combination of the compounds according to the invention with other compounds and, for example, with other antimitotic drugs (either tubulin depolymerising or stabilising), with compounds used in standard chemotherapy (such as platinum derivatives), with other retinoids (in particular 4-HPR), with epigenetic drugs (in particular HDAC inhibitors) and with drugs directed against specific targets (either tumoral or non-tumoral) (such as trastuzumab for HER2-positive breast cancer).

A further object of the invention is pharmaceutical compositions comprising at least one compound of formula (I) as active ingredient and at least one pharmaceutically acceptable carrier and/or diluent. The pharmaceutically acceptable carrier or diluent is selected on the basis of the recommended method of administration and the standard pharmaceutical technology know-how available to expert people in the field.

The compositions according to the invention can contain biologically compatible carriers suitable for administration to animals, such as saline solution, and optionally auxiliary substances such as excipients, stabilisers or diluents.

Such pharmaceutical compositions are preferably prepared in the form of a unit dose for oral, rectal, percutaneous or parenteral administration. The compounds according to the invention will be administered in a therapeutically effective quantity determinable by expert people in the field, on the basis of the patient's weight, age and state of health, the frequency of the treatment and any concomitant treatments.

If combined with other agents, the compounds according to the invention can be administered simultaneously or sequentially, in any order.

Sodium 4-aminoxyacetate-4-HPR (salt 1a) has a satisfactory ability to inhibit the growth of tumour cells (deriving from both solid and haematological tumours), which has proved similar to that of the parent drug, 4-oxo-4-HPR, in ovarian and breast cancer cell lines and in peritoneal mesothelioma, neuroblastoma and lymphoma cells (Table 1). Analysis of the mechanism of action demonstrated that salt 1a retains the specific characteristic of 4-oxo-4-HPR of inducing cell death by activating two independent pathways: the generation of ROS (pro-apoptotic activity) and the cell cycle arrest during the mitotic phase (antitubulin activity) (FIG. 1). Moreover, preliminary experiments with combined treatment demonstrate that salt 1a has a synergic activity with paclitaxel, cisplatin and 4-HPR in tumour cell lines of different histotypes (FIG. 2).

To establish whether salt 1a possesses greater solubility/bioavailability than the parent compound, in vivo experiments were conducted in murine models. The results demonstrate that the salt is far more soluble than the parent compound and reaches plasma levels up to 60 times higher than 4-oxo-4-HPR and with less variability (Table 2). Moreover, the accumulation of the compound in proximity to the inoculation site observed in the mice treated with 4-oxo-4-HPR was not found in those treated with the salt. During the experiments to determine the plasma levels of salt 1a, it was also found that the compound does not possess high toxicity for the animals when administered at daily doses of 60 and 100 mg/kg.

The antitumoral activity of salt 1a was in vivo evaluated in mice xenografted with human mesothelioma (STO), ovarian cancer (IGROV-1) and breast cancer (MDA-MB-231) cells. The activity of salt 1a on mesothelioma cells was evaluated in the first experiment: the experiment showed an activity trend of the compound, although it did not reach statistical significance (probably due to the high variability in tumour growth in the mice of the control group) (FIG. 3a). As regards to ovarian model, at the doses of 60 and 90 mg/kg, salt 1a significantly increased the survival of the mice inoculated with IGROV-1 cells ($p<0.01$), without any evident signs of severe toxicity (FIG. 3b). Finally, concerning the breast cancer model, it was observed that the dose of 90 mg/kg of salt 1a reduced tumour growth ($p=0.01$) (FIG. 3c), without evident signs of severe toxicity.

Compounds 1b (sodium 4-aminooxybutyrate-4-HPR) and 1c (sodium 4-aminooxyhexanoate-4-HPR) were also tested for antitumoral activity in vitro: the ability of both compounds to inhibit tumour growth was similar to that of sodium 4-aminooxyacetate-4-HPR (Table 3).

Compound 9-[3-(2-Amino-ethoxyimino)-2,6,6-trimethyl-cyclohex-1-enyl]-3,7-dimethylnona-2,4,6,8-tetraenoic acid (4-hydroxy-phenyl)amide (1d) was also tested in vitro for antitumoral activity. In ovarian cancer cells (A2780), compound 1d induced a cycle arrest in G2-M coupled with antiproliferative ($IC_{50}$ after 72 hours of treatment=0.9548 µM) and apoptotic (sub-G1 peak) activities.

The compounds according to the present invention wherein X is —COOH can be prepared, for example, as exemplified in the reaction scheme, by reacting compound 2 (4-oxo-4-HPR) with a suitable amino oxyacid, typically 3a-c, and sodium acetate, in a solvent such as aqueous ethanol (as described in the literature: *J. Med. Chem.* 2004, 47, 6716-6729). The compounds thus obtained are then reacted with an aqueous solution of a base, typically 0.1M sodium bicarbonate, giving salts 1a-c after the water has been removed (Scheme 1).

Scheme 1:
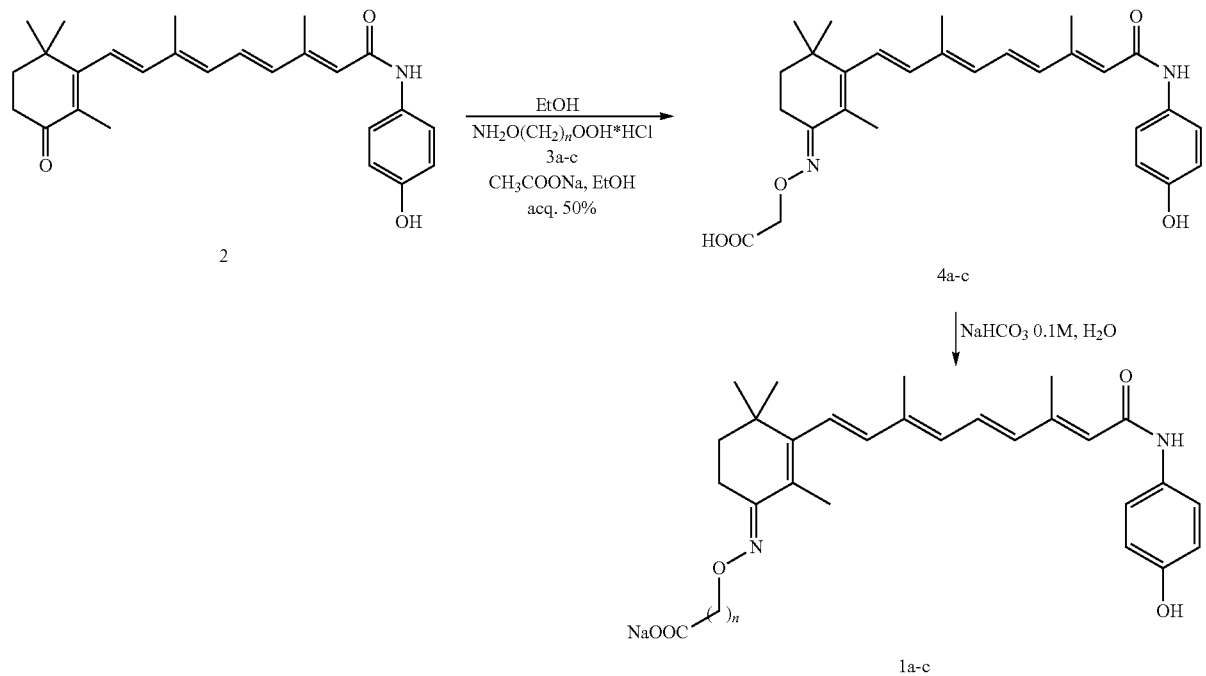
NH$_2$OCH$_2$COOH*HCl 3a commercial
NH$_2$O(CH$_2$)$_3$COOH*HCl 3b
NH$_2$O(CH$_2$)$_5$COOH*HCl 3c
Amino oxyacids 3b and 3c can be prepared by the procedures reported in schemes 2 and 3 respectively.
Scheme 2:
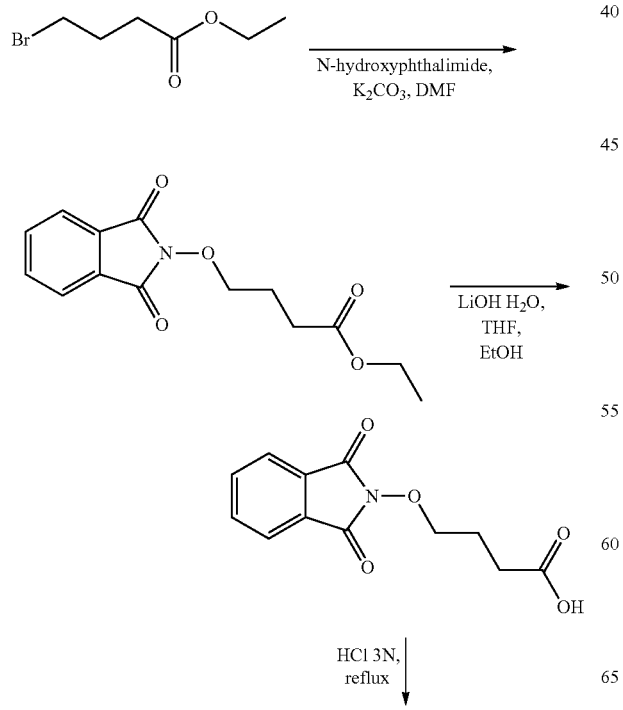
-continued
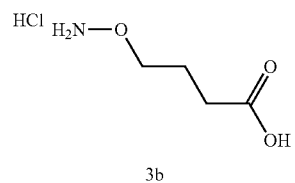
Scheme 3
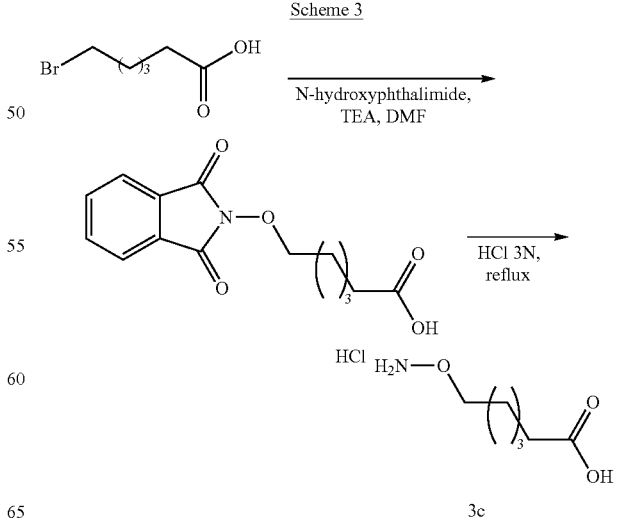

The compounds of formula (I) wherein X is NH₂ can be prepared, for example, as exemplified in the reaction scheme 4, by reacting compound 2 (4-oxo-4-HPR) with a 2-amino-alkoxyamine dihydrochloride such as 2-aminoethoxyamine and sodium acetate, in a solvent such as aqueous ethanol.

Scheme 4

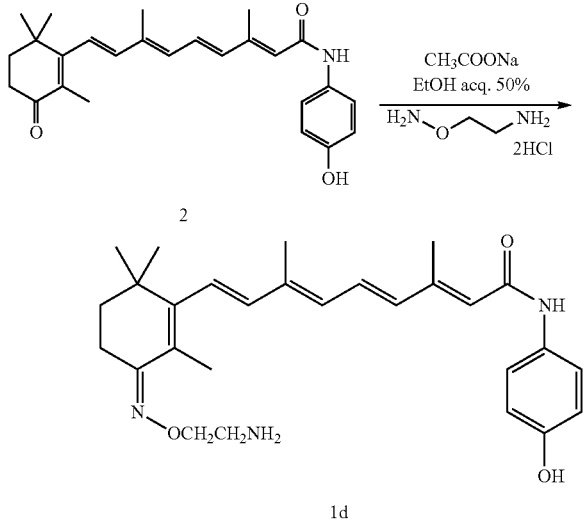

All the compounds of formula (I) can be obtained in accordance with the above reaction schemes by suitably varying the reagents and the starting compounds. The starting compounds are known or can be obtained from commercial compounds by reactions known to the skilled person.

BRIEF DESCRIPTION OF THE DRAWINGS

FIG. 1—Mechanisms of action of salt 1a.

EXAMPLES

Example 1

Figure 1:
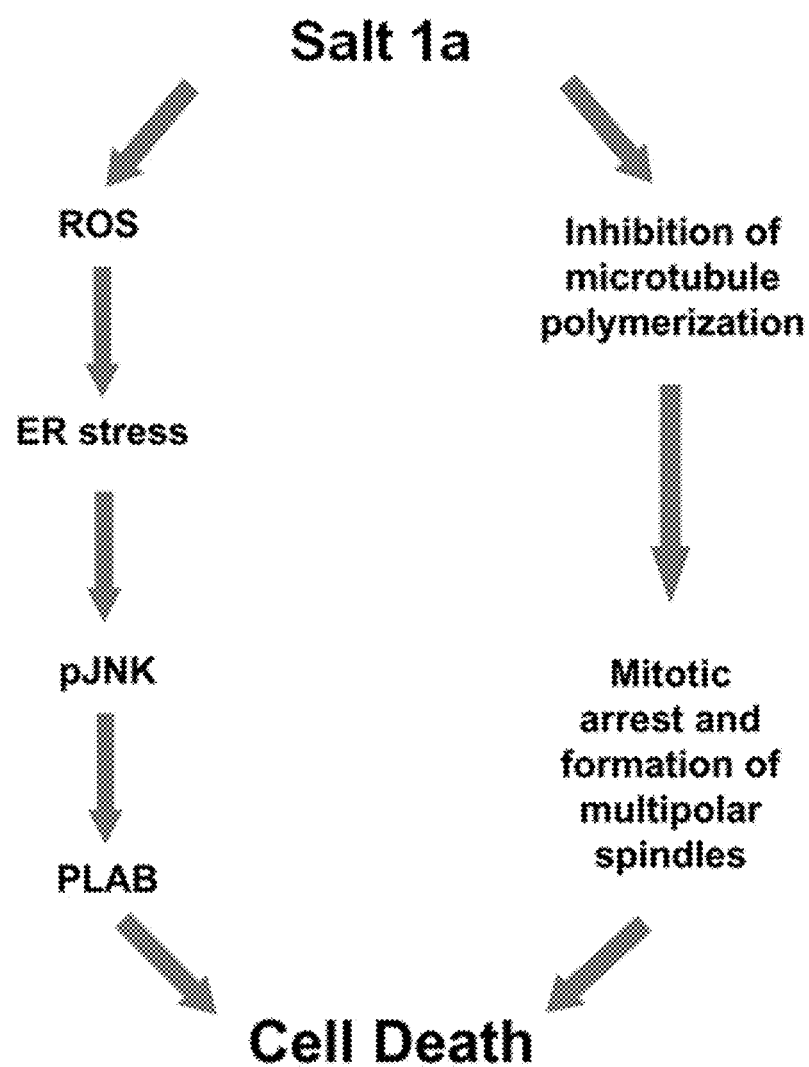

Preparation of Compound 1a 17 mL of a solution of $NH_2OCH_2COOH \cdot 1/2HCl$ (3a, 410 mg, 3.75 mmols) and $CH_3COONa$ (166 mg, 2.39 mmols) in 50% aqueous EtOH was added to a suspension of compound 2 (4-oxo-4-HPR, 700 mg, 1.73 mmols) in EtOH (11 mL). The reaction was kept under stirring at room temperature for 24 hours. The solvent was then removed at low pressure and the residue was diluted with cold $H_2O$ (20 mL), milled, and finally filtered under vacuum. 739 mg (1.54 mmols) of compound 4a (4-(carboxymethoxyimino)fenretinide) was obtained. Yield: 89%

Melting point: 121.8° C.

$^1$H-NMR (CDCl₃) δ: 7.43 (2H, d, J=8.2 Hz); 7.08 (1H, s); 6.99 (1H, dd, J=11.60; 14.6 Hz); 6.82 (2H, d, J=8.2 Hz); 6.44-6.16 (4H, m); 5.82 (1H, s); 5.32 (2H, s); 2.72 (2H, t, J=6.4 Hz); 2.44 (3H, s); 2.04 (3H, s); 1.91 (3H, s); 1.65 (2H, t, J=6.4); 1,12 (6H. s).

$^1$H-NMR (DMSO-d₆) δ: 9.78 (1H, s); 9.16 (1H, bs); 7.42 (2H, J=8.24 Hz); 7.05-6.89 (1H, m); 6.68 (2H, d, J=8.24); 6.47-6.24 (4H, m); 6.00 (1H, s); 4.57 (2H, s); 2.67-2.55 (2H, m); 2.33 (3H, s); 2.00 (3H, s); 1.82 (3H, s); 1.82 (3H, s); 1.63-1.49 (2H, m); 1.07 (6H, s).

15.4 mL of an 0.1N solution of NaHCO₃ was added to a suspension of 4a (739 mg, 1.54 mmols) in 10 mL of H₂O The reaction was left under stirring for about 22 hours. The solvent was then removed at low pressure. 760 mg (1.52 mmols) of compound 1a was obtained. Yield: 99%

Melting point: 188.6° C. (with dec.)

$^1$H-NMR (DMSO-d₆) δ: 9.8 (1H, s); 9.38 (1H, bs); 7.42 (2H, d, J=8.2 Hz); 6.97 (1H, dd, J=14.3; 11.60 Hz); 6.68 (2H, d, J=8.2 Hz); 6.44-6.24 (4H, m); 6.01 (1H, s); 4.12 (2H, s); 2.61-2.53 (2H, m); 2.32 (3H, s); 2.00 (3H, s); 1.82 (3H, s); 1.58-1.47 (2H, m); 1.05 (6H, s).

Example 2

Preparation of Compound 1b 0.5 mL of a solution of 3b (17 mg, 0.11 mmols) and CH₃COONa (5 mg, 0.07 mmols) in 50% aqueous EtOH was added to a suspension of compound 2 (20 mg, 0.05 mmols) in EtOH (0.5 mL). The reaction was kept under stirring at room temperature for 24 hours. The solvent was removed at low pressure, the residue was taken up with ethyl acetate, and the solution was washed with H₂O and dried on Na₂SO₄. The crude product was then purified by preparative chromatography in CH₂Cl₂: CH₃OH 95: 5. 20 mg (0.04 mmols) of compound 4b was obtained.

(4-(carboxypropoxyimino)fenretinide) (yellow glass). Yield: 80%

$^1$H-NMR (CDCl₃) δ: 7.39 (2H, m); 7.12 (1H, s); 6.96 (1H, dd, J=10.6, 14.4); 6.78 (2H, m); 6.37-6.14 (4H, m); 5.80 (1H, s); 4.18 (2H, t, J=6.0) 2.60 (2H, t, J=6.6); 2.50 (2H, t, J=7.3); 2.41 (3H, s); 2.07-1.97 (2H, m); 2.02 (3H, s); 1.90 (3H, s); 1.89-1.76 (2H, m); 1.07 (6H, s).

280 μL of an 0.1N solution of NaHCO₃ was added to a suspension of 4b (18 mg, 0.035 mmols) in 0.5 mL of H₂O. The reaction was left under stirring for about 20 hours. The solvent was then removed at low pressure. 15 mg (0.028 mmols) of compound 1b (4-(carboxypropoxyimino) fenretinide sodium salt) was obtained. Yield: 81%.

$^1$H-NMR (DMSO-d₆) δ: 9.80 (1H, s); 7.40 (2H, m); 6.95 (1H, dd, J=11.4, 14.4); 6-66 (2H, m); 6.42-6.24 (4H, m); 5.99 (1H, s); 3.97 (2H, t, J=6.5); 2.31 (3H, s); 1.98 (3H, s); 1.92-1.79 (2H, m); 1.83 (3H, s); 1.79-1.63 (2H, m); 1.51 (2H, t, J=7.2); 1.04 (6H, s).

Preparation of Compound 3b (4-aminooxybutyric acid hydrochloride): ethyl 4-(1,3-dioxo-1,3-dihydroisoindol-2-yloxy)butyrate.

N-hydroxyphthalimide (1.11 g, 6.64 mmols) and K₂CO₃ (1.84 g, 13.28 mmols) were added to a solution of ethyl 4-bromobutyrate (1 mL, 6.64 mmols) in anhydrous DMF (6.5 mL). The solution was left under stirring at room temperature overnight. When the solvent had been evaporated, the reaction mixture was taken up with ethyl acetate and washed with a saturated solution of NaCl. The organic phase was dried on Na₂SO₄ and the solvent was evaporated. The product was crystallised from isopropanol (1.67 g). Yield: 91%.

Melting point: 48.5° C.

$^1$H-NMR (DMSO-d$_6$) δ: 7.86 (4H, m); 4.16 (2H, t, J=6.4); 4.07 (2H, t, J=7.0); 2.53 (2H, t, J=7.3); 1.97-1.84 (2H, m); 1-19 (3H, t, J=7.0).

4-(1,3-dioxo-1,3-dihydroisoindol-2-yloxy)butyric acid.

A solution of LiOH.H$_2$O (0.8 g, 19.1 mmols) in ethanol (5.8 mL) and H$_2$O (5.8 mL) was added to a solution of ethyl 4-(1,3-dioxo-1,3-dihydroisoindol-2-yloxy)-butyrate (1.65 g, 5.97 mmols) in THF (18 mL), and the solution was left to react at room temperature overnight. When the solvents had been evaporated, a 6N solution of HCl (6 mL) was added and the crude product was extracted with ethyl acetate. The combined organic phases were washed with a saturated solution of NaCl and dried with Na$_2$SO$_4$. The product was then crystallised from ethyl acetate. 1.1 g of product was obtained. Yield: 74%.

$^1$H-NMR (DMSO-d$_6$) δ: 11.25 (1H, bs); 7.83 (1H, d, J=7.0); 7.65-7.48 (2H, m); 7.39 (1H, d, J=7.3); 3.89 (2H, d, J=7.3); 2.4 (2H, t, J=7.3); 1.89-1.74 (2H, m).

4-aminooxy-butyric acid hydrochloride. A suspension of 4-(1,3-dioxo-1,3-dihydro-isoindol-2-yloxyloxy)-butyric acid (400 mg, 1.61 mmols) in a solution of 3N HCl (2 mL) was heated to reflux for 2 hours. The phthalic acid was filtered, the filtrate was evaporated, and the product was crystallised from methanol. 166 mg of product 3b was obtained. Yield: 66%.

Melting point: 140° C.

$^1$H-NMR (DMSO-d$_6$) δ: 10.89 (3H, bs); 4.00 (2H, d, J=6.4); 2.31 (2H, t, J=7.3); 1.88-1.73 (2H, m).

Bibliography: Cyclic hydroxamates, especially multiply substituted [1,2]oxazinan-3-ones, Wolfe, Saul et al. Canadian Journal of Chemistry, 81(8), 937-960; 2003; Method for the synthesis of oxazinone amino acid derivatives, Wolfe, Saul et al. PCT Int. Appl., 2003018565, 6 Mar. 2003.

Example 3

Preparation of Compound 1c 0.65 mL of a solution of 3c (27 mg, 0.15 mmols) and CH$_3$COONa (7 mg, 0.1 mmols) in 50% aqueous EtOH was added to a suspension of compound 2 (30 mg, 0.07 mmols) in EtOH (0.56 mL). The reaction was placed under stirring at room temperature for 24 hours. The solvent was removed at low pressure, the residue was taken up with ethyl acetate, and the solution was washed with H$_2$O and dried on Na$_2$SO$_4$. The crude product was then purified by preparative chromatography in CH$_2$Cl$_2$:CH$_3$OH 95:5. 16 mg (0.03 mmols) of compound 4c (4-(carboxypentoxyimino) fenretinide) was obtained. Yield: 43%

$^1$H-NMR (CDCl$_3$) δ: 7.41 (2H, m); 7.14 (1H, s); 7.07-6.90 (1H, m); 6.80 (2H, m); 6.41-6.13 (4H, m); 5.82 (1H, s); 4.12 (2H, t, J=6.1); 2.62 (2H, t, J=6.4); 2.49-2.3 (2H, m); 2.43 (3H, s); 2.03 (3H, s); 1.92 (3H, s); 1.82-1.40 (8H, m); 1.09 (6H, s).

280 μL of an 0.1N solution of NaHCO$_3$ was added to a suspension of compound 4c (15 mg, 0.028 mmols) in 0.5 mL of H$_2$O. The reaction was left under stirring for about 20 hours. The solvent was then removed at low pressure. 11 mg (0.02 mmols) of compound 1c was obtained. Yield: 71%.

$^1$H-NMR (DMSO-d$_6$) δ: 9.84 (1H, s); 7.40 (2H, m); 7.02-6.86 (1H, m); 6.66 (2H, m); 6.44-6.23 (4H, m); 6.00 (1H, s); 3.98 (2H, t, J=6.0); 2.31 (3H, s); 2.11-2.03 (2H, m); 1.98 (3H, s); 1.83 (3H,s); 1.83 (3H,s); 1.88-1.74 (2H, m); 1.64-1.34 (2H, m); 1.32-1.17 (2H, m)1.03 (6H, s).

Preparation of Compound 2c (6-aminooxy hexanoic acid):

6-(1,3-dioxo-1,3-dihydro-isoindol-2-yloxy)-hexanoic acid. N-hydroxy-phthalimide (2.44 g, 15 mmols) and triethylamine (6.3 ml, 45 mmols) were added to a solution of 6-bromohexanoic acid (3 g, 15 mmols) in anhydrous DMF (30 mL). The solution was left under stirring at ambient temperature for 48 hours. The precipitate formed was filtered, and when the solvent had been evaporated the crude product was purified on Sephadex LH-20 with a 3:1:1 mixture of hexane:acetone: ethyl ether. 2.2 g of product was obtained. Yield: 53%.

$^1$H-NMR (CDCl$_3$) δ: 7.95-7.68 (4H, m); 4.23 (2H, t, J=6.4); 2.43 (2H, t, J=7.0); 1.93-1.68 (4H, m); 1.67-1.51 (2H, m).

6-aminooxy-hexanoic acid. A suspension of 6-(1,3-dioxo-1,3-dihydro-isoindol-2-yloxy)-hexanoic acid (120 mg, 0.43 mmols) in a solution of 3N HCl (2 mL) was heated to reflux for 3 hours. The precipitate was removed by filtration, the water was evaporated, and the product was crystallised from methanol. 66 mg of product 3b was obtained. Yield: 84%.

$^1$H-NMR (DMSO-d$_6$) δ: 10.88 (3H, bs); 3.95 (2H, t, J=6.3); 2.18 (2H, t, J=7.3); 1.62-1.41 (4H, m); 1.36-1.20 (2H, m).

Example 4

Preparation of Compound 1d

A suspension of compound 2 (23 mg, 0.05 mmoli) in ethanol (500 μL) was treated with a solution of 2-aminoethoxyamine dihydrochloride (16 mg, 0.11 mmol) and anhydrous sodium acetate (6 mg, 0.07 mmol) in 50% aqueous ethanol (500 μL). The resulting mixture was stirred at room temperature for 24 h. The solvent was removed under reduced pressure and the crude was purified by preparative RP-18 chromatography in CH$_3$OH/H$_2$O 9:1 to give 18 mg of compound 1d. Yield: 76%. mp 134° C.

$^1$H-NMR (CH$_3$OH-d$_4$) δ: 7.37 (2H, d, J=8.5 Hz), 7.05 (1H, dd, J=11.3, 14.6), 6.74 (2H, d, J=8.5), 6.48-6.20 (4H, m), 5.99 (1H, s), 4.33-4.25 (2H, m), 3.28-3.22 (2H, m), 2.70 (2H, t, J=6.41 Hz), 2.37 (3H, s), 2.04 (s, 3H), 1.91 (3H, s), 1.62 (2H, t, J=6.4).

Example 5

Pharmacological Experiments

Experiments In Vitro

Figure 2:
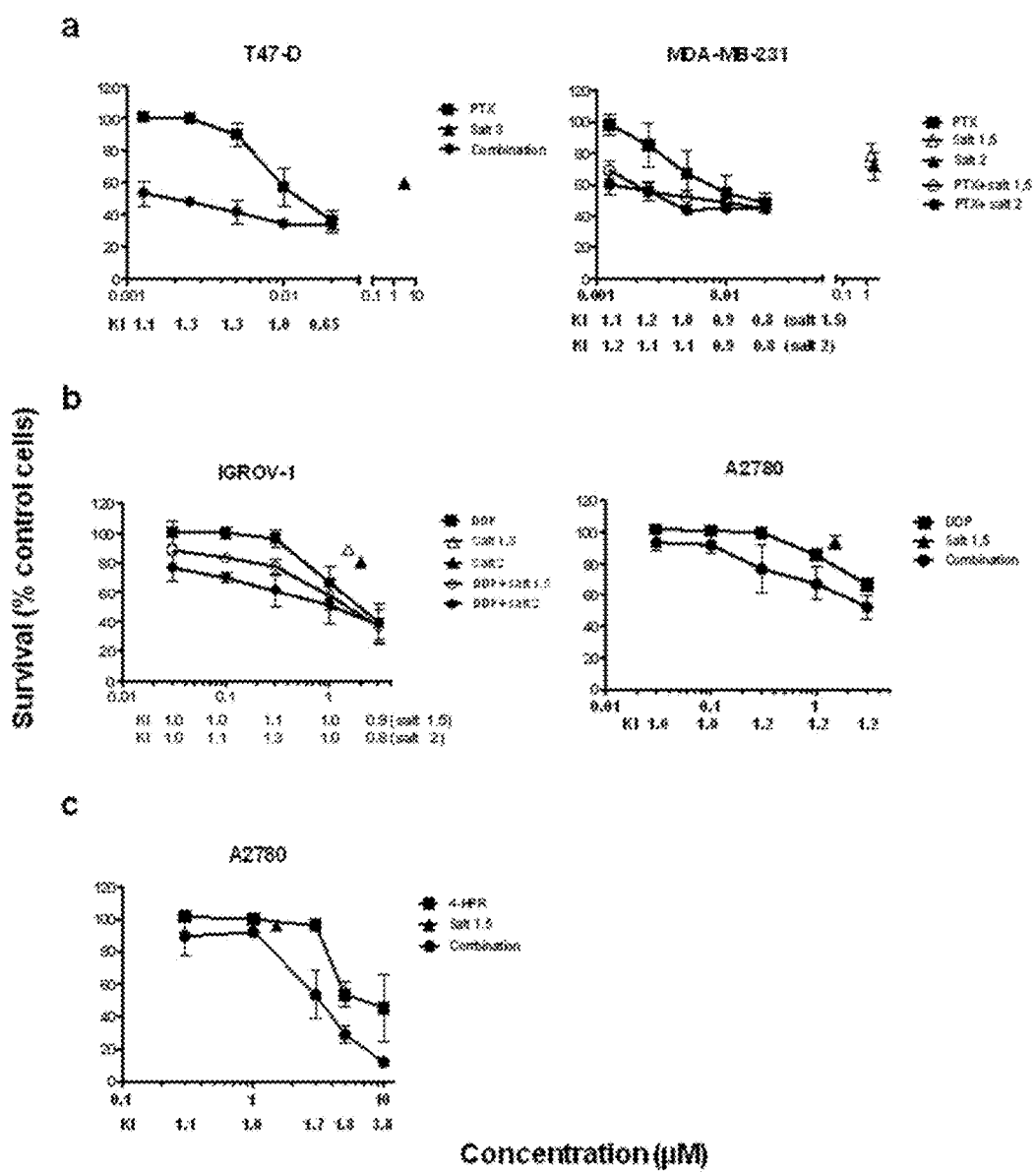
FIG. 2—Antiproliferative activity of the combined treatment of salt 1a with a) paclitaxel (PTX); b) cisplatin (DDP); or c) fenretinide (4-HPR).

The antiproliferative activity of the various compounds 1a-c (in both monotherapy and combined treatment) on the different tumour cell lines was evaluated by sulphorhodamine B assay after 72 hours of treatment, and the dose able to inhibit 50% of growth (IC$_{50}$) was calculated for the monotherapy (the results are summarized in Table 1 and Table 3), while the Kern Index (KI) was determined as the synergism/antagonism refractive index for the combined treatment (the results are depicted in FIG. 2).

As regards to the evaluation of the mechanism of action, ROS generation was determined after 5 hours of treatment with the use of the 5-(and -6)-chloromethyl-2', 7'-dichloro-dihydrofluorescein diacetate (CM-H2DCFDA) probe, while the cell cycle was evaluated by staining with propidium iodide. Cytofluorimetric analysis (FACS) was conducted in both cases.

Experiments In Vivo

To evaluate the plasma levels of salt 1a, 4-oxo-4-HPR (120 mg/kg) and salt 1a (sodium 4-aminoxyacetate-4-HPR) (60 and 100 mg/kg) were administered i.p. to nude mice for 4 consecutive days (once a day), and the plasma levels were evaluated by HPLC 5 hours after the last administration (the results are summarized in Table 2).

Figure 3:
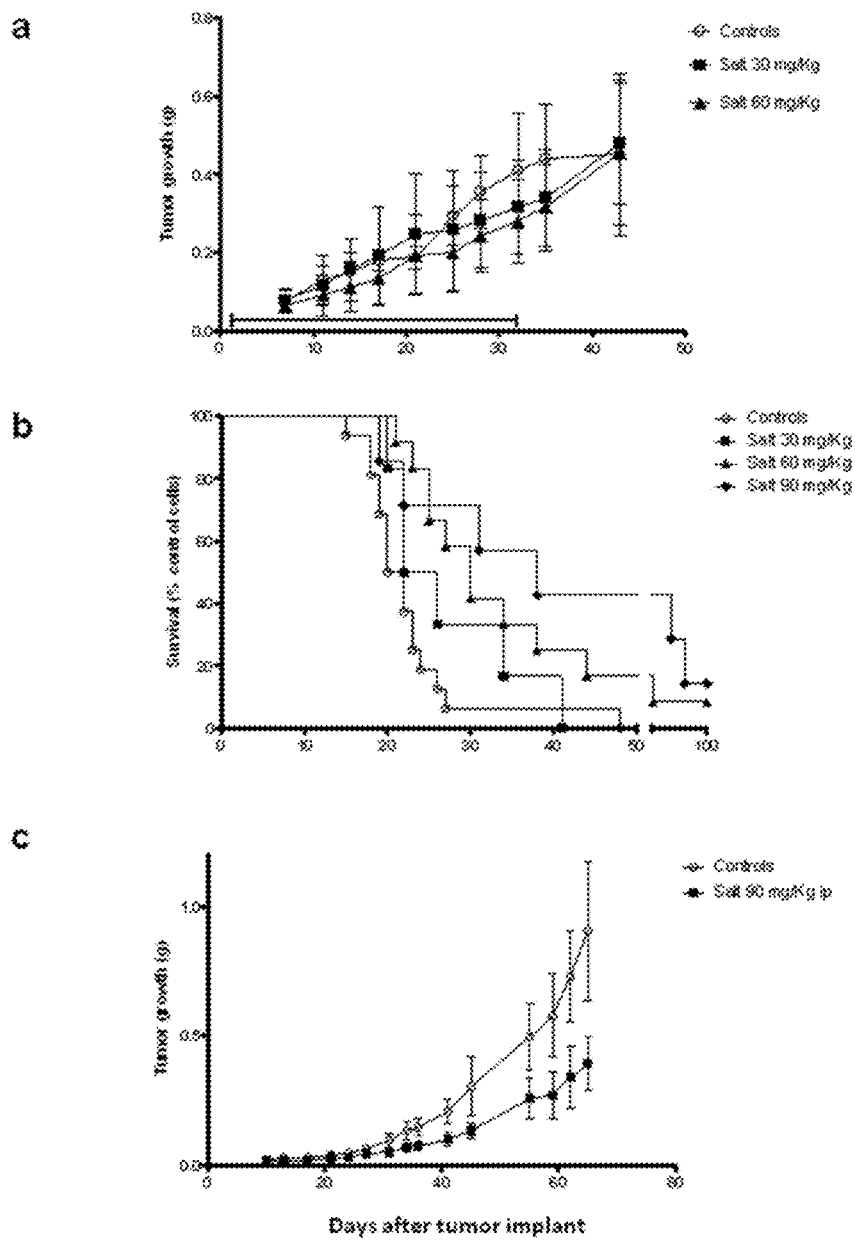
FIG. 3—In vivo antitumor activity of salt 1a in a) mesothelioma cells (STO); b) ovarian cancer cells (IGROV-1); and c) breast cancer cells (MDA-MB-231).

As regards to mesothelioma, the mice were inoculated s.c. with STO cells, and treatment with the salt 1a began one day after tumor cell inoculation (doses: 30 and 60 mg/kg i.p.; 5 days/week for 4 weeks). The control mice were treated with the same solvent as used to dissolve the salt. The animals were examined twice a week to check their weight and any signs of toxicity. Tumour growth in the various groups (control and treated) was evaluated, and the differences were statistically analysed (the results are shown in FIG. 3a).

For the ovarian model, nude mice were inoculated i.p. with IGROV-1 cells, and treatment with the salt 1a began one day after tumor cell inoculation (doses: 30, 60 and 90 mg/kg i.p.; 5 days/week for 4 weeks). The control mice were treated with the same solvent as used to dissolve the salt. The animals were examined twice a week to check their weight and any signs of toxicity. The survival time of the various groups (control and treated) was evaluated, and the differences were statistically analysed. The experiments were conducted in duplicate, and comparable results were obtained (the results are shown in FIG. 3b).

As regards the breast cancer model, human breast cancer cells (MDA-MB-231) were inoculated into the mammary fat pad of NOD/SCID-gamma mice, and treatment with the salt 1a began one week after tumor cell inoculation (dose: 90 mg/kg; 4 days/week for 5 weeks). The animals were examined twice a week to check their weight and any signs of toxicity. Tumour growth in the various groups (control and treated) was evaluated, and the differences were statistically analysed. The experiments were conducted in duplicate, and comparable results were obtained (the results are shown in FIG. 3c).

TABLE 1

Antiproliferative activity of salt 1a in different tumour cell lines

| Tumour cell line | IC$_{50}$ (μM) |
|---|---|
| Ovary | |
| A2780 | 2.78 |
| IGROV-1 | 3.82 |
| SKOV-3 | 5.96 |
| Breast | |
| T47-D | 3.95 |
| MDA-MB-231 | 3.97 |
| BT-474 | 3.69 |
| Neuroblastoma | |
| SK-N-BE | 1.55 |
| SK-N-SH | 1.9 |
| Sk-N-5Y | 1.3 |
| Mesothelioma | |
| STO | 1.48 |
| MESO | 1.28 |
| Lymphoma | |
| JVM-2 | 1.11 |

TABLE 2

In vivo plasma levels

| Compound | Dose | Plasma level |
|---|---|---|
| 4-oxo-4-HPR | 120 mg/Kg | 0.8 μM ± 0.4 |
| Salt 1a | 60 mg/Kg | 60.3 μM ± 2.52 |
| Salt 1a | 100 mg/Kg | 63.7 μM ± 2.08 |

4-oxo-4-HPR: 5% DMSO, 5% cremophor, H$_2$O.
Salt 1a: 5% DMSO, H$_2$O.

TABLE 3

Antiproliferative activity of salts 1b (LOM1098) and 1c (LOM1133) in different tumour cell lines

| Tumour cell line | IC$_{50}$ (μM) | |
|---|---|---|
| | LOM1098 | LOM1133 |
| Ovary | | |
| A2780 | 3.59 | 2.37 |
| IGROV-1 | 3.54 | 2.19 |
| Breast | | |
| T47-D | 4.20 | 3.00 |
| MDA-MB-231 | 4.26 | 2.95 |

The invention claimed is:

1. A compound of the following formula (I), or a pharmaceutically acceptable salt thereof:

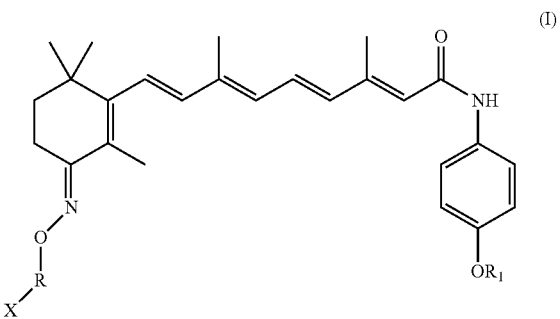

wherein:
X is —COOH or NH$_2$;
R is a straight or branched C$_1$-C$_{10}$ alkylene chain; and
R$_1$ is H, straight or branched C$_1$-C$_{10}$ alkyl, aryl, or R$_2$CO—, wherein R$_2$ is straight or branched C$_1$-C$_{10}$ alkyl.

2. The compound of formula (I), or a pharmaceutically acceptable salt thereof according to claim 1, wherein X is —COOH.

3. The salt of a compound of formula (I) according to claim 2 selected from an alkali or alkaline-earth metal, an organic amine or an amino acid.

4. The salt of a compound of formula (I) according to claim 3 selected from sodium, potassium, lithium, calcium or magnesium.

5. The compound of formula (I), or a pharmaceutically acceptable salt thereof according to claim 1, wherein X is NH$_2$.

6. The compound of formula (I), or a pharmaceutically acceptable salt thereof according to claim 1, wherein R is a straight or branched C$_1$-C$_6$ alkylene chain.

7. The compound of formula (I), or a pharmaceutically acceptable salt thereof according to claim 1, wherein $R_1$ is H.

8. A compound of formula (I) according to claim 1 selected from the group consisting of:
- sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxyacetate (compound 1a);
- sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxybutyrate (compound 1b); and
- sodium 2-[3-[(1E,3E,5E,7E)-9-(4-hydroxyanilino)-3,7-dimethyl-9-oxo-nona-1,3,5,7-tetraenyl]-2,4,4-trimethyl-cyclohex-2-en-1-ylidene]amino]oxyhexanoate (compound 1c).

9. A medicament comprising the compound of formula (I), or a pharmaceutically acceptable salt thereof according to claim 1.

10. An antitumoral agent comprising the compound of formula (I) or a pharmaceutically acceptable salt thereof according to claim 1.

11. A method for treatment of breast cancer, ovarian cancer, prostate cancer, colorectal cancer, mesothelioma and other sarcomas, neuroblastoma, lymphoma, leukaemia or melanoma, comprising providing and applying an effective amount of the antitumoral agent according to claim 10 in a patient in need thereof.

12. A combination of a compound of formula (I) according to claim 1, with one or more medicaments selected from the group consisting of antimitotic agents, compounds used in standard chemotherapy, natural or synthetic retinoids, epigenetic drugs, and (tumoral or non-tumoral) target-specific medicaments.

13. A pharmaceutical composition comprising at least one compound of formula (I) according to claim 1 as active ingredient and a pharmaceutically acceptable carrier and/or eluent.

14. The compound of formula (I) or a pharmaceutically acceptable salt thereof according to claim 2, wherein R is a straight or branched $C_1$-$C_6$ alkylene chain.

15. The salt of a compound of formula (I) according to claim 3, wherein R is a straight or branched $C_1$-$C_6$alkylene chain.

16. The salt of a compound of formula (I) according to claim 4, wherein R is a straight or branched $C_1$-$C_6$alkylene chain.

17. The compound of formula (I), or a pharmaceutically acceptable salt thereof according to claim 5, wherein R is a straight or branched $C_1$-$C_6$ alkylene chain.

18. The compound of formula (I), or a pharmaceutically acceptable salt thereof according to claim 2, wherein $R_1$ is H.

* * * * *